United States Patent

Vukán et al.

[11] Patent Number: 5,978,692
[45] Date of Patent: Nov. 2, 1999

[54] APPARATUS FOR EXAMINING ELECTROCHEMICAL EFFECTS OF IN VIVO METAL IMPLANTS CAUSING ALLERGIC SYMPTOMS AND/OR INFLAMMATION IN A LIVING ORGANISM

[75] Inventors: György Vukán; Zoltán Vass; Zoltán Kriskó; László Kiss; Laura Sziráki; Magda Lakatosné Varsányi, all of Budapest, Hungary

[73] Assignee: Dentimpex Kft., Hungary

[21] Appl. No.: 08/952,205

[22] PCT Filed: May 7, 1996

[86] PCT No.: PCT/HU96/00026

§ 371 Date: Feb. 10, 1998

§ 102(e) Date: Feb. 10, 1998

[87] PCT Pub. No.: WO96/35373

PCT Pub. Date: Nov. 14, 1996

[30] Foreign Application Priority Data

May 9, 1995 [HU] Hungary ................ P9501355

[51] Int. Cl.[6] ........................... A61B 5/05
[52] U.S. Cl. .................... 600/345; 600/556
[58] Field of Search .................. 600/345, 372, 600/556

[56] References Cited

U.S. PATENT DOCUMENTS 4,040,129  8/1977  Steinemann et al.
5,415,164  5/1995  Faupel .................. 600/372

FOREIGN PATENT DOCUMENTS

WO 86/06265  11/1986  WIPO.
WO 89/00400   1/1989  WIPO.

Primary Examiner—Eric F. Winakur
Attorney, Agent, or Firm—Finnegan, Henderson, Farabow, Garrett & Dunner, LLP

[57] ABSTRACT

An apparatus for examining the electrochemical effects of (in vivo) metal implants causing allergic symptoms and/or inflamation in living organism, the apparatus containing two probes and a signal processing circuit connected thereto. One of the probes is a reference electrode (1) provided with reference electrolyte (34), which is connected to the soma tissue near the implant while the other probe is a measuring electrode (2) provided with a metal contact tip (6) to be contacted with the implant. The reference electrode (1) and the measuring electrode (2) are connected through an amplifier (20, 27) to one of the inputs of a comparing unit (22, 28). The other input of the comparing unit (22, 28) is connected the output of a memory (24, 30) containing data concerning the metal to be examined, and one of the outputs of the comparing unit (22, 28) is connected the display for the measured data (11).

8 Claims, 4 Drawing Sheets

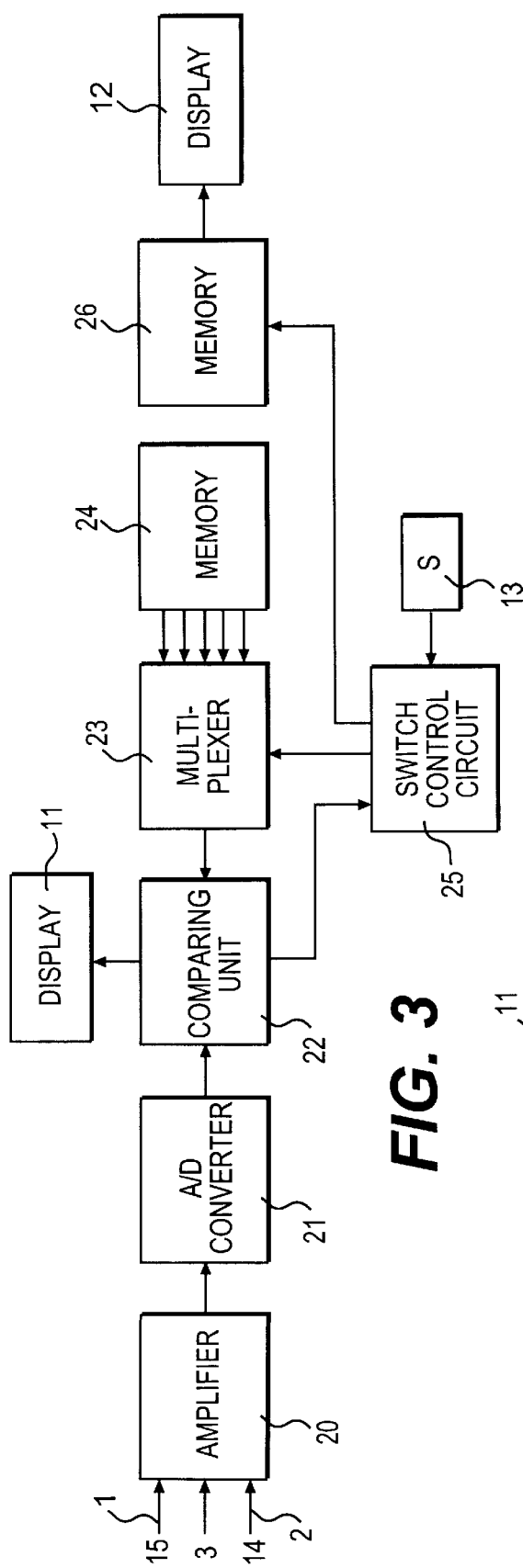
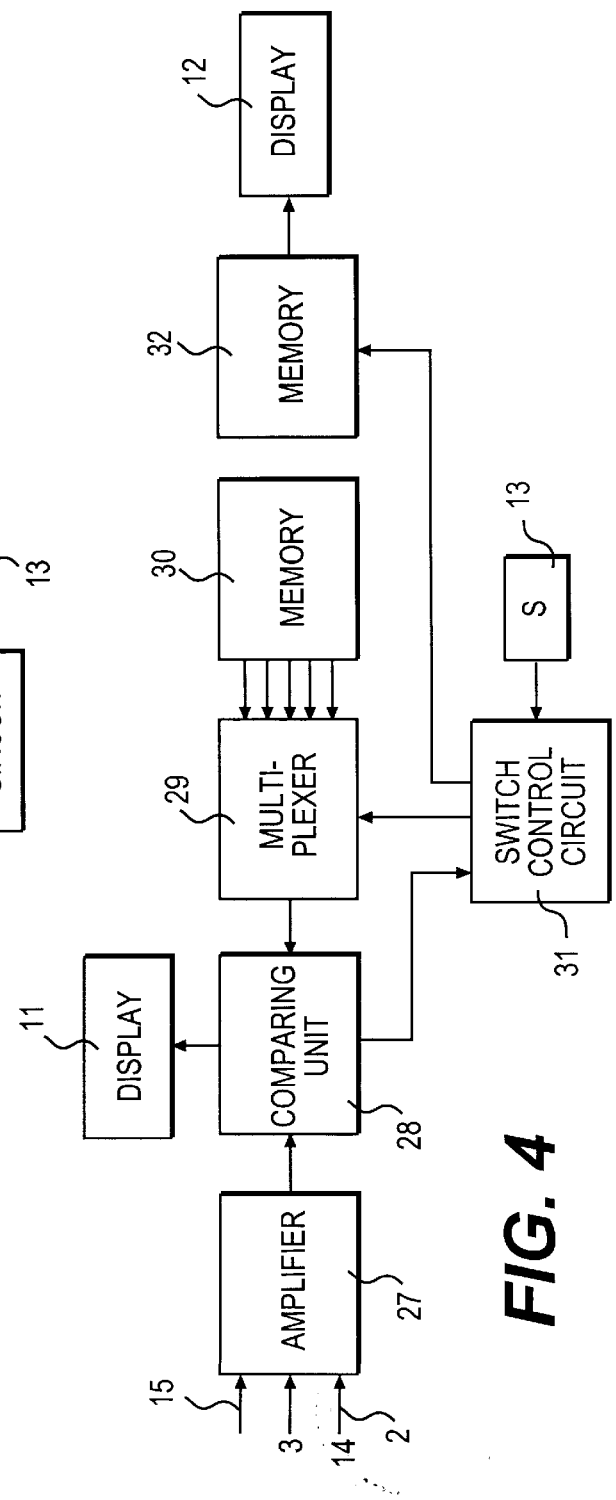
FIG. 3
FIG. 4

APPARATUS FOR EXAMINING ELECTROCHEMICAL EFFECTS OF IN VIVO METAL IMPLANTS CAUSING ALLERGIC SYMPTOMS AND/OR INFLAMMATION IN A LIVING ORGANISM

BACKGROUND OF THE INVENTION

1. Field of the Invention

The invention relates to an apparatus for examining the electrochemical effects of in vivo metal implants causing allergic symptoms and/or inflammation in a living organism.

2. Description of the Related Art

Recent research has demonstrated that metal implants in living organism can cause allergic symptoms as a result of ionic migration from the metal alloys implanted in vivo toward the living tissues. These migrated ions easily connect to protein bodies at the temperature of the human body. As a result, in the organism already implanted with metal, allergic symptoms can appear, i.e. local or long-distance mucosal and cutaneous reactions, eczema, dermatitis, dermatosis, etc. Under certain circumstances, this effect can cause extraordinary serious altercations, and the risk exists until the anaphylactogemic factor, i.e. the metal implants which can be dental prosthesis, filling of a tooth, screw, nail, etc., is removed from the organism.

HU-PS 192 218 describes a method and apparatus for exploring and examining such effects. By use of the mentioned apparatus and method, potential difference is measured between the implanted metal alloys and, at the same time, ion currents effected by the potential difference are measured in vivo in the neighboring soma tissues. For making the measurement, a specially formed measuring probe is applied, the current values are measured by a current/potential (I/U) converter connected to the measuring probe, and by a signal processing unit connected thereto, then displayed.

It has been found in practice that during the application of the mentioned known apparatus, the ion migration causing the harmful effects cannot be explored to the extent necessary. During the application, it has been also demonstrated that the measured values cannot be reproduced consistently, and that the measurements obtained are influenced by numerous parameters and by chance as well. Also, the measuring unit is embedded in a relatively large instrument case, so that its application becomes difficult. A further problem is that more than one person is required to perform the measurement, to accomplish suitable location of the probes and their connection, and for reading the measured values on the instrument.

WO 89100400 describes a solution where the reference electrode is integral part of the apparatus and, as such, the reference electrode cannot be releasably connected to the apparatus. Neither the reference electrode, nor the measuring electrode can be made as a disposable article.

A further serious disadvantage of both mentioned solutions is to meet the requirements of hygienic regulations, which, considering the spreading of the newer epidemic-like diseases, become increasingly strict with respect to handling of instruments and apparatuses used during medical treatment. In the case of this known solution, the sterilization of the apparatus embedded in the instrument cannot be operated in accordance with the regulations.

SUMMARY OF THE INVENTION

The aim of the invention is partly to eliminate the disadvantages of the mentioned known solutions and partly to develop an apparatus, which, on the one hand, performs the electrochemical examination of the metal implants in vivo more accurately and reliably, and on the other hand, the apparatus processing the measured data can be handled easily and meet all the requirements of the latest hygienic regulations as well.

In electrochemistry, it is well known that every metal and every metal alloy can be determined by the so called anodic polarization curve. On the basis of that curve, it can be seen on which potential no metal dissolution can be found in given medium, the potential value above which chloride containing solution pitting corrosion attack begins, and where the metal dissolution is expected. Thus, in the case of the metals as well as metal alloys used for metal implants, the anodic polarization curve provides an indication of which cases an undesirable effect can occur.

The invention is based on the recognition that if the potential difference is measured not between two metal implants in vivo, but between a metal implant and a reference electrode palpating the neighboring soma tissue, so that there is no need for measuring the current, more accurate, more reliable and predictably reproducible measurements can be obtained. For each case of applying metal or metal alloy, the corrosion potential can be determined, and the range can be predetermined, within which, pitting corrosion or metal dissolution can occur.

The essential recognition is in that taking into consideration only recent dental practice, several kinds of new materials have been appeared, for which it cannot be known exactly whether they have an anaphylactogenic effect or not, because neither the measuring method applied up to now, nor its accuracy enables this knowledge.

The main task to be solved by the invention is an apparatus for examining by potential measuring the electrochemical effect of the implanted metal substitutions (in vivo) causing allergic symptoms and/or inflammation in the living organism.

The potential difference is measured between the implanted metal and the reference electrode palpating neighboring soma tissue.

The measured potential difference is compared with the corrosion potential values, obtained in vitro for the metal implants and it is also preferred according to the invention, if it is determined that a potential difference concerning the given metal is higher than a predetermined limit value indicating the initial stage of the dissolution of that metal.

It is also advantageous, if light or sound signal indicate if the potential difference higher than the limit value.

Besides the above, it is preferred that if before the final implantation, a sample of the same implant-material to be implanted, is either contacted to the implantation place to be expected or arranged there expediently for a period of 24–28 hours, and then the potential difference is measured.

The object of the invention is an apparatus for examining electrochemical effects induced by in vivo metal implants that may cause allergic symptoms and/or inflammation in a living organism. The apparatus comprises a reference probe having a reference electrode and a reference electrolyte, a measuring probe having a measuring electrode provided with a metal contact tip, a signal processing circuit connected to the reference and measuring probes and including an amplifier, a comparing unit having two inputs and an output, a memory for storing data concerning the implanted metal and having a memory output, and a data display, one of the two inputs of the comparing unit being connected to the amplifier, the other of the two inputs of the comparing unit being connected the memory output, and the output of the comparing unit being connected the data display.

The reference probe comprises a handle and an axially aligned headpiece having opposite ends. The headpiece is connected releasably at one the opposite ends to the handle through an electric contact on the handle and connected to a line connected to the amplifier. The other of the opposite ends of the headpiece supports a plastic tube containing electrolyte, an absorbent element impregnated with the electrolyte is arranged in the plastic tube and protrudes from the plastic tube as the reference electrode, and a the metal part in the headpiece connects the electrolyte in the plastic tube to electric contact on the handle. The measuring probe includes a measuring headpiece having opposite ends, one of the opposite ends is connected releasably to a measuring handle through an electric contact associated with a start switch in the measuring handle, and a metal contacting tip projects from the other of the opposite ends of the measuring head piece.

Preferably, the headpiece of the reference probe includes an electrolyte tank and the plastic tube has one end protruding from the tank, an opposite end located in the electrolyte tank at a distance from the metal part, and a separating layer covering the opposite end. The metal part includes an electrically non-conducting pricking element to penetrate the separating layer.

It is advantageous, if the head element of the reference probe is provided with a lock cap.

In a further preferred embodiment according to the invention, the headpiece is provided with a cover.

It is advantageous in the sense of the invention if the headpiece and the handle are connected to each other by bayonet joint or the headpiece and the handle are connected to each other by breaking joint.

In a further preferred embodiment according to the invention the headpiece is disposable.

It is advantageous if the electrolyte is of colloidal get state.

It is advantageous finally if the measuring apparatus is embedded in a dental column.

BRIEF DESCRIPTION OF THE DRAWINGS

The invention is described in detail with the aid of the enclosed drawings presenting the embodiment of the solution according to the invention by way of example, in which:

FIG. 3 is a block diagram of a possible embodiment of the apparatus according to the invention;

FIG. 4 is a block diagram of another possible embodiment of the apparatus according to the invention; while

DESCRIPTION OF THE PREFERRED EMBODIMENTS

Figure 1A:
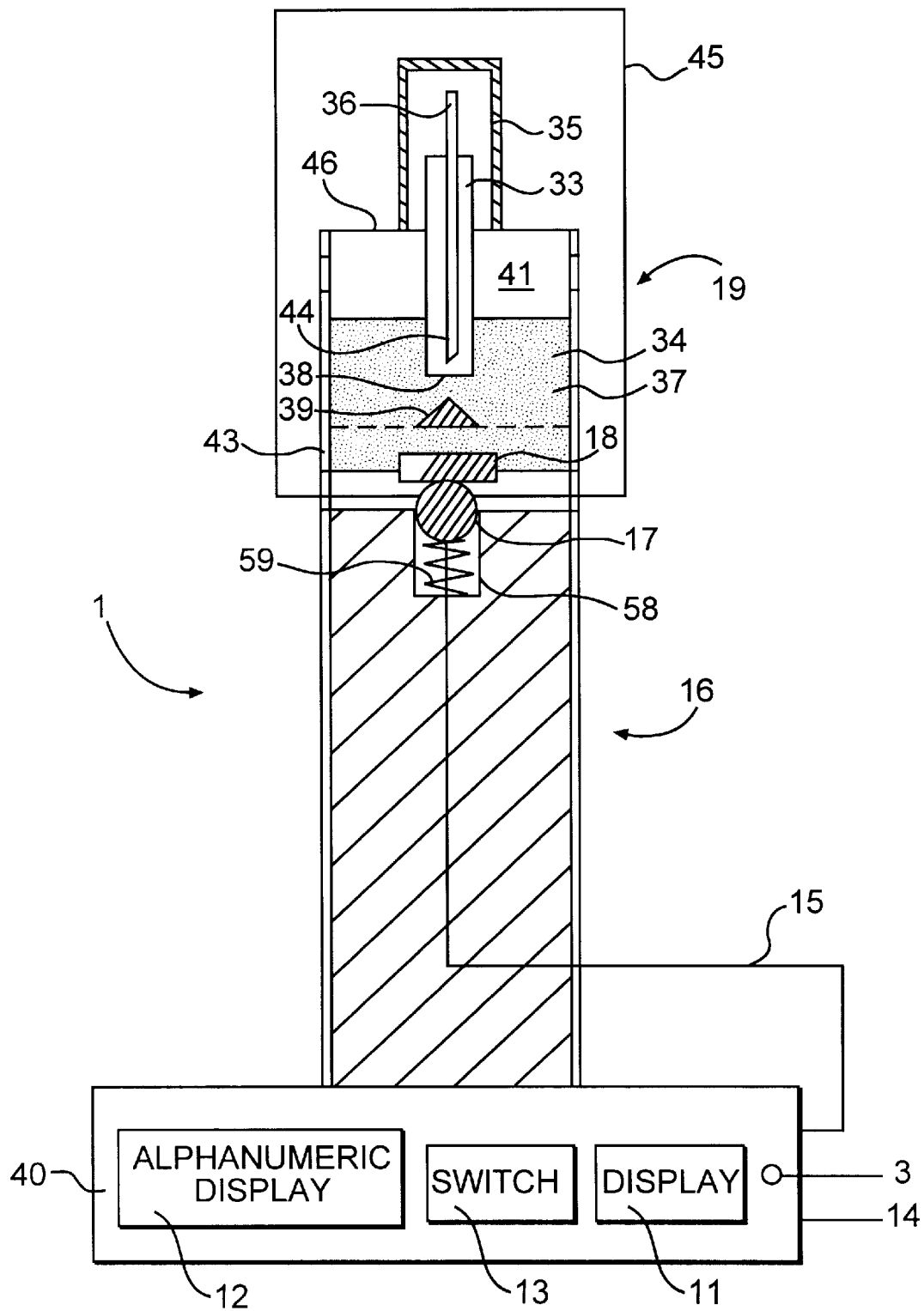
FIG. 1a is a cross-section illustrating a possible embodiment of the reference electrode according to the invention for palpating the tissue connected to the apparatus.

FIG. 1a illustrates in section a possible embodiment of a reference electrode 1 according to the invention for palpating the tissue, which is connected to the measuring instrument 40 according to the invention. The reference electrode 1 has two main parts, i.e. a handle 16 and a headpiece 19, which are releasably connected to each other and placed in a mantle-like cover. The measuring instrument 40 is connected to the handle 16 containing a conductive line 15 connected between the measuring instrument 40 and an electric contact 17 for connection of the line 15 to the headpiece 19. The contact 17 can be, for example, a spheroidal element supported by a spring 59 in a groove 58 formed in the handle 16.

The head piece 19 is provided with a metal contact 18 for connecting electrically to the spherical contact 17 on the one hand, and, on the other hand, with an electrolyte 34 provided in a tank 43. The electrolyte is saturated salt solution, i.e. NaCl solution, preferably in a gel state. In the electrolyte 34, on the symmetrical axis of the headpiece 19, is an insulated tube 33 containing a cloth-like absorbent or wick element 44 for absorbing the electrolyte 34. Preferably, the element 44 extends from the projecting end of the tube 33 through a paper coot protruding from the tube 33 as a head element 36 for palpating tissue. On the end of the tube 33 facing the contact 18 is a separating layer 38 for separating the tube 33 from the electrolyte 34. At a given distance from the separating layer 38, and between the separating layer 38 and the metal part 18, an electrically non-conducting—insulating—pricking element 39 is arranged so that its tip faces in the direction of the separating layer 38. The tube 33 is mounted in the headpiece 19 by a joining element 41 so that it is able to move in it axially in response to pressure. The joining element 41 can be filled for example by sterilized air. One part of the tube 33 also protrudes on the mantle-like cover 46 of the headpiece 19. Thus, the electrolyte 34 is absorbed into the tube 33 at all times. In order to observe the absorption of the electrolyte 34, it is preferred that the electrolyte is mixed with an electrically non-conducting indifferent color material 37. In this way, the coloring of the protruding part of the tube 33 indicates the absorbing of the electrolyte 34 for the doctor, which is the condition required for the electric conduction.

The headpiece 19 is provided with a cover 45 enabling it to be insulated from the surroundings under sterilized circumstances up to the time of utilization. The headpiece 19, itself, is disposable, that is, after use it can be throw away. To this end, the headpiece 19 and the handle 16 are joined releasably to each other either by threaded connection, or bayonet joint, or simply by a breakable joint. This embodiment is preferred because, in the examination by a dentist, the headpiece 19 contacts the oral cavity of the patient. During the measurement, the reference electrode 1 should contact with the soma tissue, for example, with the mucosa of the patient. It is considered as a reference condition, i.e. that the measurements could be reproduced. According to the experience, the mucosa or other soma tissues can be considered as a stable measuring point.

Figures 1B, 2:
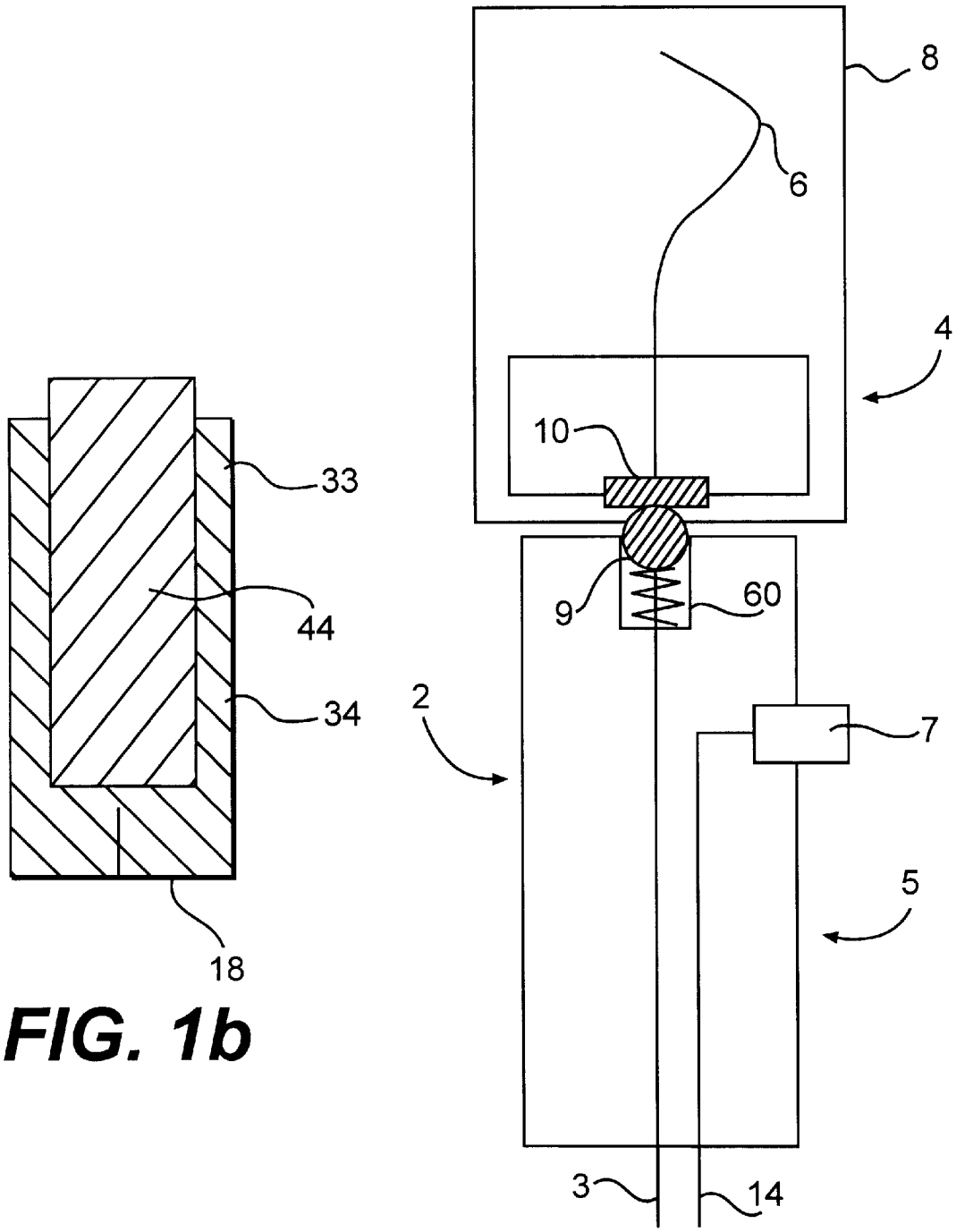
FIG. 1b illustrates an other embodiment of the headpiece of the reference electrode in section according to the invention for palpating the tissue.
FIG. 2 shows an embodiment of the measuring electrode also in section.

FIG. 1b illustrates another embodiment of the headpiece 19 in section, wherein the plastic tube 33, the tank 43 containing the electrolyte 34, as well as the absorbent element 44 are formed as a single element, i.e. in the tube 33, an absorbent element 44 impregnated with the electrolyte 34 is arranged. This embodiment is extraordinarily simple, and the plastic tube prevents evaporation of the electrolyte 34.

FIG. 2 shows also in section, an embodiment of the measuring electrode 2 for contacting metal applicable to use of the measuring instrument 40 according to the invention. The measuring electrode 2 should be contacted with previously dried metal implants, for example, an over-denture in the mouth. The measuring electrode 2 also has two parts, i.e. a headpiece 4 having a contact probe tip 6 and a handle 5 connected releasably to each other, and they are embedded expediently in a cylindrical case. The handle 5 contains a line 3 for joining to the measuring instrument 40 and forwarding the measured signal, an electric contact 9 ensuring the connection of the line 3 to the headpiece 5, and a line 14 provided with a start switch 7. The contact 9 can be a spheroidal element, for example, which is resiliently supported by a spring 60 in a groove 61 formed in the handle 5. The electrical contact 9 is arranged coaxially in the handle 5. The headpiece 4 contains a cylindrical lock-cap 8, on the end of which facing towards the handle 5, a metal contact element 10 is centrally formed, one side of which touches the contact 9. On the other side of the contact element 10, a metal contact tip 6 is provided, which is hermetically sealed, in sterile way by the lock cap 8. In this way, the headpiece 4 can be formed as a disposable element as well, and the measurement can be performed while excluding the possibility of infection.

The possible embodiments shown in FIGS. 1*a*, 1*b*, and 2 can be applied expediently for dental and dental surgery purposes. For the examination of the effects induced by other metal implants, further embodiments can be realized. For examination of metal implants in the body, the metal contact tip 6 should be formed to the appropriate length and formation for the applicable conditions. Similarly, the head element 36 of the headpiece 19, for palpating the tissue, should be formed also in conformance with the soma tissue to be measured.

In the case of a possible embodiment of the evaluating measuring instrument 40 in which the reference electrode 1 is arranged in the handle 16, the result of the measurements is indicated on a display 11, either a visible LED display, for example, or an audible sound signal, while the reference values are shown on the alphanumerical display. In addition, the measuring instrument 40 is provided with a switch element 13 for intermittent operation as well.

The arrangement itself can be formed so that the measuring instrument is embedded into a separate measuring case or into the column of the dental chair. In this latter case, however, it is preferred that the display 11 is an alphanumerical display 12 or is formed with the headpiece 16 of the reference electrode 1 or as a unit with the headpiece of the measuring electrode 2.

The measuring instrument 40 itself can be realized with both analogue and digital circuits.

In FIG. 3 a possible embodiment of the measuring instrument 40 is shown with digital circuits. The line 15 of the reference electrode 1 for palpating the soma tissue, and the lines 3 and 14 of the measuring electrode 2 contacting the metal implants provide means for passing measured potential difference is through the amplifier 20, the output of which is connected to the input of the A/D converter 21, the output of which, in turn, is connected to one of the inputs of the comparing unit 22, while to the other input of the comparing unit 22, the output of the multiplexer 23 is joined. The output of the comparing unit 22 is coupled with the display 11 on the one hand, and on the other hand with one of the inputs of the switch control circuit 25. The inputs of the multiplexer 23 are connected to the outputs of the memory 24 while its control input is joined to one of the outputs of the switch control circuit 25. The so-called dangerous potential values concerning the metals and metal alloys to be examined are fed in the memory 24. The selection of the data relating the metal or metal alloy just examined takes place by the aid of the switch control circuit 25, the other input of which is coupled with the switch element 13. The limit values are set up in the memory 24 to correspond to the potential considered as harmful, which exceeds, for example, the positive value of +150 to +200 mV at the corrosion potential for Ni-based alloys. Naturally, the limit value can be determined for all the metals even in the case where the reference electrode 1 is made of other material. One output of the switch control circuit 25 is connected to the input of the memory 26, the output of which is joined to the input of the alphanumerical display 12.

FIG. 4 represents the possible embodiment of the measuring instrument 40 according to the invention, which is realized by analogue circuits. The line 15 of the reference electrode 1 palpating the soma tissue, and the lines 3 and 14 of the measuring electrode 2 palpating the metal, measure the potential difference through an amplifier 27, the output of which is connected to one of the inputs of the comparing unit 28, while the other input of the comparing unit 28 is joined to the output of the multiplexer 29. One of the outputs of the comparing unit 28 is connected to the display 11, while its other output is joined to one of the inputs of the switch control circuit 31. The inputs of the multiplexer 29 are connected to the outputs of the analogue memory 30, while its control input is joined to the other input of the switch control circuit 31. The potential data value concerning the metals and metal alloys to be measured and considered as dangerous, are fed in the memory 30. The selection of the implant to be measured is taken place by the switch control circuit 31, which is coupled with the switch element 13. The individual limit values are set in the memory 30 on the previously described way. One output of the switch control circuit 31 is also connected to the input of the memory 32, the output of which is led to the input of the alphanumerical display 12. It is expedient, firstly to keep in view the shock-proof prescriptions, secondly for the sake of simple handling, to utilize some kind of battery as power supply unit.

Figure 5:
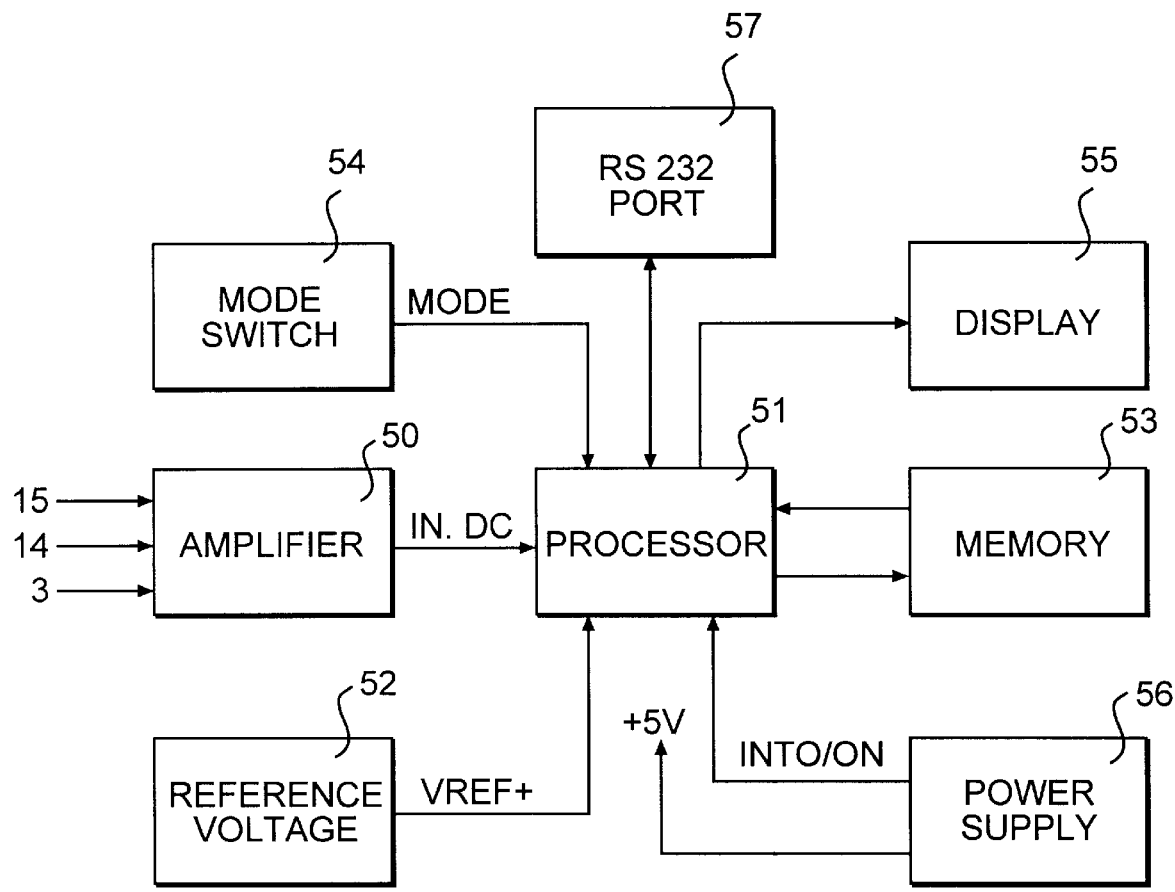
FIG. 5 is a block diagram showing a further possible embodiment of the apparatus according to the invention.

A further possible embodiment of the measuring instrument 40 according to the invention can be seen on FIG. 5.

The line 15 of the reference electrode 1 and the lines 3 and 14 of the measuring electrode 2 are connected to the input of the amplifier 50 having high input resistance, in order to join the direct current voltage (D.C. voltage) coming from the reference electrode 1 and the measuring electrode 2 to the input A/D converter of the processor 51 connected to the output of the amplifier 50. The input points are expediently provided with diode protection. The applied amplifiers are formed with low noise levels and low drift circuits. To the output of the processor 51 is joined the display 55, expediently LCD display, one of its control inputs is connected to the operation mode switch 54, while its other input joins to the supply unit 56, its further input-, output channel is connected to the memory field 53 and a RS 232 port 57. The processor 51 is in conjunction with the reference voltage source 52 as well.

The task of the latest embodiment, is to ensure the requested temperature for the A/D conversion as well as the reference potential values being independent from supply voltage. The task of the memory fields 53 is to store the operating program and potentials in table form. The measured values are written in EEPROM. The measured values with serial numbering are stored or in a given case, together with a preselected international tooth identification or other identification number as well. Each identification number contains the data of tooth or of an interior organ, of the material of implants and that of the data concerning the limit potential. The task of the operation switch 54 is to put into operation the apparatus, to select the given potential limit value and to start the measuring. The display 55 displays the set and measured value.

During the measurement, firstly the reference potential concerning the implants to be measured is selected by means of either the switch control circuit 31 or the operation mode switch 54, then the reference electrode 1 is pressed onto the soma tissue near the implant to be measured, observing that the electrolyte 34 is absorbed in the absorbent element 44, respectively. In the case of the embodiment wherein the reference electrode 1 is provided with a headpiece 19 impregnated with electrolyte 34, it is simply pressed onto the soma tissue. Then the measuring electrode 2 is pressed onto the metal implant to be measured and the potential difference between the reference electrode 1 and the measuring electrode 2 is measured.

If the measured value considering the characteristic corrosion potential of Ni-based alloys shows a difference of about from +150 to +200 mV, then it is considered as pathologic in the case of the reference electrode 1 of Ag/AgCl. The potential values can be determined by known way for every metal or metal alloy.

The solution according to the invention can be applied advantageously, for example, in the dental practice for both diagnostic and prognostic purposes as well as in the surgery before implanting the implant. By the aid of this, it can be examined whether the over-denture can cause allergic or inflamation symptoms, or it can be determined before implanting the implant whether it can cause problems in the future.

We claim:

1. Apparatus for examining electrochemical effects induced by in vivo metal implants that may cause allergic symptoms and/or inflammation in a living organism, comprising:

a reference probe having a reference electrode and a reference electrolyte;

a measuring probe having a measuring electrode provided with a metal contact tip;

a signal processing circuit connected to the reference and measuring probes and including an amplifier, a comparing unit having two inputs and an output, a memory for storing data concerning the implanted metal and having a memory output, and a data display, one of the two inputs of the comparing unit being connected to the amplifier, the other of the two inputs of the comparing unit being connected to the memory output, and the output of the comparing unit being connected the data display to provide an indicated comparison of measured value with data stored in the memory;

wherein the reference probe comprises a handle and an axially aligned headpiece having opposite ends, the headpiece is connected releasably at one of the opposite ends to the handle through an electric contact on the handle and connected to a line connected to the amplifier, the other of the opposite ends of the headpiece supports a plastic tube containing the reference electrolyte, an absorbent element impregnated with the reference electrolyte is arranged in the plastic tube and protrudes from the plastic tube as the reference electrode, and a metal part in the headpiece connects the reference electrolyte in the plastic tube to the electric contact on the handle, and wherein the measuring probe includes a measuring headpiece having opposite ends, one of the opposite ends is connected releasably to a measuring handle through an electric contact associated with a start switch in the measuring handle, and the metal contact tip projects from the other of the opposite ends of the measuring head piece and is connected to a line connected to the amplifier.

2. The apparatus of claim 1, wherein the headpiece of the reference probe includes an electrolyte tank and the plastic tube has one end protruding from the tank, an opposite end located in the electrolyte tank at a distance from the metal part, and a separating layer covering the opposite end, and wherein the metal part includes an electrically non-conducting pricking element to penetrate the separating layer.

3. The apparatus of claim 1, wherein the absorbent element arranged in the plastic tube and protruding from the plastic tube as the reference electrode is provided with a lock cap.

4. The apparatus of claim 1, wherein the headpiece of the reference probe is provided with a cover.

5. The apparatus of claim 1, wherein the headpiece and the handle of the reference probe are connected to each other by a bayonet joint.

6. The apparatus of claim 1, wherein the headpiece and the handle of the reference probe are connected to each other by a breaking joint.

7. The apparatus of claim 1, wherein the headpiece of the reference probe is disposable.

8. The apparatus of claim 1, wherein the headpiece of the measuring probe is disposable.

* * * * *